(12) United States Patent
Scanlon

(10) Patent No.: US 10,272,207 B2
(45) Date of Patent: Apr. 30, 2019

(54) FRONT CAP FOR A MEDICAMENT DELIVERY DEVICE

(71) Applicant: Carebay Europe Ltd, Sliema (MT)

(72) Inventor: Gerard Scanlon, Stockholm (SE)

(73) Assignee: SHL Medical AG, Zug (CH)

( * ) Notice: Subject to any disclaimer, the term of this patent is extended or adjusted under 35 U.S.C. 154(b) by 174 days.

(21) Appl. No.: 14/902,156

(22) PCT Filed: Mar. 13, 2014

(86) PCT No.: PCT/EP2014/055021
§ 371 (c)(1),
(2) Date: Dec. 30, 2015

(87) PCT Pub. No.: WO2014/154498
PCT Pub. Date: Oct. 2, 2014

(65) Prior Publication Data
US 2016/0144132 A1 May 26, 2016

(30) Foreign Application Priority Data

Mar. 25, 2013 (SE) ...................................... 1350375

(51) Int. Cl.
*A61M 5/32* (2006.01)
(52) U.S. Cl.
CPC ........ *A61M 5/3204* (2013.01); *A61M 5/3202* (2013.01)
(58) Field of Classification Search
CPC .............. A61M 5/3213; A61M 5/3202; A61M 2005/3215; A61M 5/3204; A61M 5/3205
See application file for complete search history.

(56) References Cited

U.S. PATENT DOCUMENTS

| 5,810,784 A * | 9/1998 | Tamaro ............... A61M 5/3275 128/919 |
| 9,028,451 B2 | 5/2015 | Jennings |
| 2007/0173772 A1 | 7/2007 | Liversidge |

(Continued)

FOREIGN PATENT DOCUMENTS

| CN | 101489610 A | 4/2009 |
| WO | 2007/138296 A1 | 12/2007 |

(Continued)

OTHER PUBLICATIONS

EPO, Int'l Search Report in PCT/EP2014/055021, dated Jun. 26, 2014.

(Continued)

*Primary Examiner* — Kami A Bosworth
*Assistant Examiner* — Alexandra Lalonde
(74) *Attorney, Agent, or Firm* — McDonnell Boehnen Hulbert & Berghoff LLP

(57) ABSTRACT

A front cap for a medicament delivery device having proximal and distal ends is configured to be releasably connected to the medicament delivery device and includes a shield grabber support and a shield grabber for connecting the front cap to an outer surface of a needle shield of a syringe positioned within the medicament delivery device. The shield grabber is coupled to the shield grabber support such that the shield grabber is axially movable relative to the shield grabber support.

10 Claims, 5 Drawing Sheets

(56) References Cited

U.S. PATENT DOCUMENTS

| | | | | |
|---|---|---|---|---|
| 2012/0191047 A1* | 7/2012 | Raday | ............... | A61M 5/2033 |
| | | | | 604/198 |
| 2014/0243753 A1* | 8/2014 | Bostrom | ............ | A61M 5/3202 |
| | | | | 604/198 |
| 2014/0330203 A1* | 11/2014 | McLoughlin | ........... | A61M 5/20 |
| | | | | 604/131 |

FOREIGN PATENT DOCUMENTS

| | | |
|---|---|---|
| WO | 2012/101629 A1 | 8/2012 |
| WO | 2012103140 A1 | 8/2012 |
| WO | 2013/006119 A1 | 1/2013 |
| WO | WO 2013006119 A1 * 1/2013 .......... A61M 5/3202 |

OTHER PUBLICATIONS

Search Report issued in Swedish Patent Application No. 1350375-0 dated Nov. 20, 2013.
Search Report issued in Taiwanese Patent Application No. 103110488 dated Aug. 30, 2016.
Search Report issued in Chinese Patent Application No. 2014800252138 dated Feb. 22, 2017.

* cited by examiner

FRONT CAP FOR A MEDICAMENT DELIVERY DEVICE

CROSS-REFERENCE TO RELATED APPLICATIONS

This is the National Stage filing under 35 U.S.C. 371 of the International Application PCT/EP2014/055021 filed Mar. 13, 2014, which claims priority under 35 U.S.C. 119 (a-d) to SE1350375-0 filed Mar. 25, 2013.

FIELD OF THE INVENTION

The present invention relates to a front cap for a medicament delivery device, especially for a disposable auto injector.

BACKGROUND OF THE INVENTION

The invention concerns auto injectors which are loaded with a container subassembly, such as a syringe, and a removable needle shield and a needle shield removing assembly provided in a cap of the injector are known in the prior art. WO-2012/101629 discloses an injector in which the cap comprises an outer portion which a user can grasp during use and an inner portion which is arranged to interact with the needle cover provided on the needle of the syringe such that when a user engages the outer portion and removes it from the injector, the inner portion will mesh with the needle cover, thus removing it from the needle of the syringe. A drawback with that prior art is that the construction of the inner portion of the cover removal assembly restricts it to be used in combination with rigid needle shields (RNS) whereas it is often that needle shields (FNS) are used.

SUMMARY OF THE INVENTION

It is therefore an object of the invention to provide a front cap for an injection device with improved qualities. In particular, it is an object of the present invention to provide a front cap that can be used together with needle shields.

Thus, in accordance with an aspect of the present invention, there is provided a front cap for a medicament delivery device having a proximal end and a distal end. The front cap is configured to be releasably connected to the medicament delivery device. Further, the front cap has an internal shield grabber support and a shield grabber for connecting the front cap to an outer surface of a needle shield of a syringe which is positioned within said medicament delivery device. The shield grabber is coupled to the internal shield grabber support such that said shield grabber is axially moveable relative to the shield grabber support.

Moreover, the shield grabber support is axially movable between a distal and a proximal end position. By providing a shield grabber that is axially moveable relative the shield grabber support, and thus the cap and the rest of the medicament delivery device to which the cap is attached, it is achieved a more shock-proof medicament delivery device. In many prior art medicament delivery devices, the shield grabber arrangements are fixedly arranged within the cap. The syringe, typically having a glass medicament container, is normally not rigidly mounted within a housing of the medicament delivery device due to tolerance variations between the parts, thus creating a certain amount of play between the syringe and the housing. If such medicament delivery device is e.g. dropped onto the floor, or otherwise subjected to an impact, especially to a rear end thereof, the syringe will move inside the housing. The distance of movement will correspond to the amount of play. If the shield grabber is rigidly arranged in the cap, the movement of the syringe could cause the needle shield to come loose from the needle, thus compromising the sterility of the needle. The front cap of the present invention further has the advantage of allowing the use of needle shields.

In accordance with an embodiment of the present invention, the distal end position is defined by a protruding element provided at the shield grabber and a stop surface provided at the shield grabber support against which said protruding element abuts in said distal end position.

In accordance with an embodiment of the present invention, the proximal end position is defined by an abutment surface provided on an inner side of the shield grabber support against which an end surface of the shield grabber abuts in said proximal end position.

In accordance with an embodiment of the present invention, the shield grabber support has a generally hollow cylindrical cross-section and wherein said abutment surface is provided in the form of a circular surface on an inner surface of the shield grabber support.

In accordance with an embodiment of the present invention, the shield grabber has a casing having a generally hollow cylindrical cross-section arranged to fit inside the hollow shield grabber support.

In accordance with an embodiment of the present invention, an inside of the shield grabber is provided with a hook element arranged to hook on to an outer surface of a needle shield. The provision of a hook element allows for the connection to the needle shield at any point of the outer surface of the needle shield, thereby making the arrangement more or less completely insensitive to tolerance variations of the different parts. This since the hook can be inserted into any portion of the outer surface of the needle shield.

In accordance with an embodiment of the present invention, the hook element comprises a tab being cut and folded inwardly from said casing. The cutting and folding saves material while still providing the desired function.

In accordance with an embodiment of the present invention, the shield grabber is made of metal. The use of metal provides for a light, durable constructional detail which can be shaped as desired and allows for a sharp hook element the can penetrate the needle shield.

In accordance with an embodiment of the present invention, a plurality of hook elements are provided. The use of a plurality of hook elements provides for a balanced construction and avoids twisting of the needle shield.

In accordance with an embodiment of the present invention, the protruding element comprises a tab being cut and folded outwardly from said casing.

The cutting and folding saves material while still providing the desired function.

In accordance with an embodiment of the present invention, a plurality of tabs are provided. The use of a plurality of tabs provides for a balanced construction and avoids twisting of the shield grabber within the shield grabber support.

In accordance with an embodiment of the present invention, the shield grabber support comprises an aperture therein and wherein a distal edge of said aperture defines said distal stop surface against which the protruding element of the shield grabber abuts in said distal end position.

In accordance with an embodiment of the present invention, the shield grabber support comprises a plurality of tongue shaped elements arranged in a generally circular manner and wherein the aperture is provided in at least one of the tongues. The provision of tongues supplies a certain amount of flexibility to the shield grabber support such that the shield grabber can be inserted into the shield grabber support and as the shield grabber reaches what is defined as the distal end position, the tongues snap back and the shield grabber is retained within the shield grabber support.

In accordance with an embodiment of the present invention, the distance which the shield grabber can move between the proximal end position and the distal end position is 0.5 to 4 mm.

In accordance with an embodiment of the present invention, the distance which the shield grabber can move between the proximal end position and the distal end position is 1 to 2 mm. This typically represent an adequate amount of play between the shield grabber and the shield grabber support to be able to counteract the play between the syringe and the medicament delivery device In accordance with an embodiment of the present invention, the shield grabber is arranged to be inserted into the shield grabber support and secured therein by a snap-fit.

In accordance with another aspect of the invention, there is provided a medicament delivery device comprising a syringe having a medicament container and a needle and a needle shield. The medicament delivery device further comprises a drive mechanism arranged to act on a plunger in the medicament container for expelling a medicament and a front cap according to any of the previous claims.

BRIEF DESCRIPTION OF THE DRAWINGS

The invention will now be described in more detail and with reference to the appended drawings in which.

DESCRIPTION OF PREFERRED EMBODIMENTS

Figure 1:
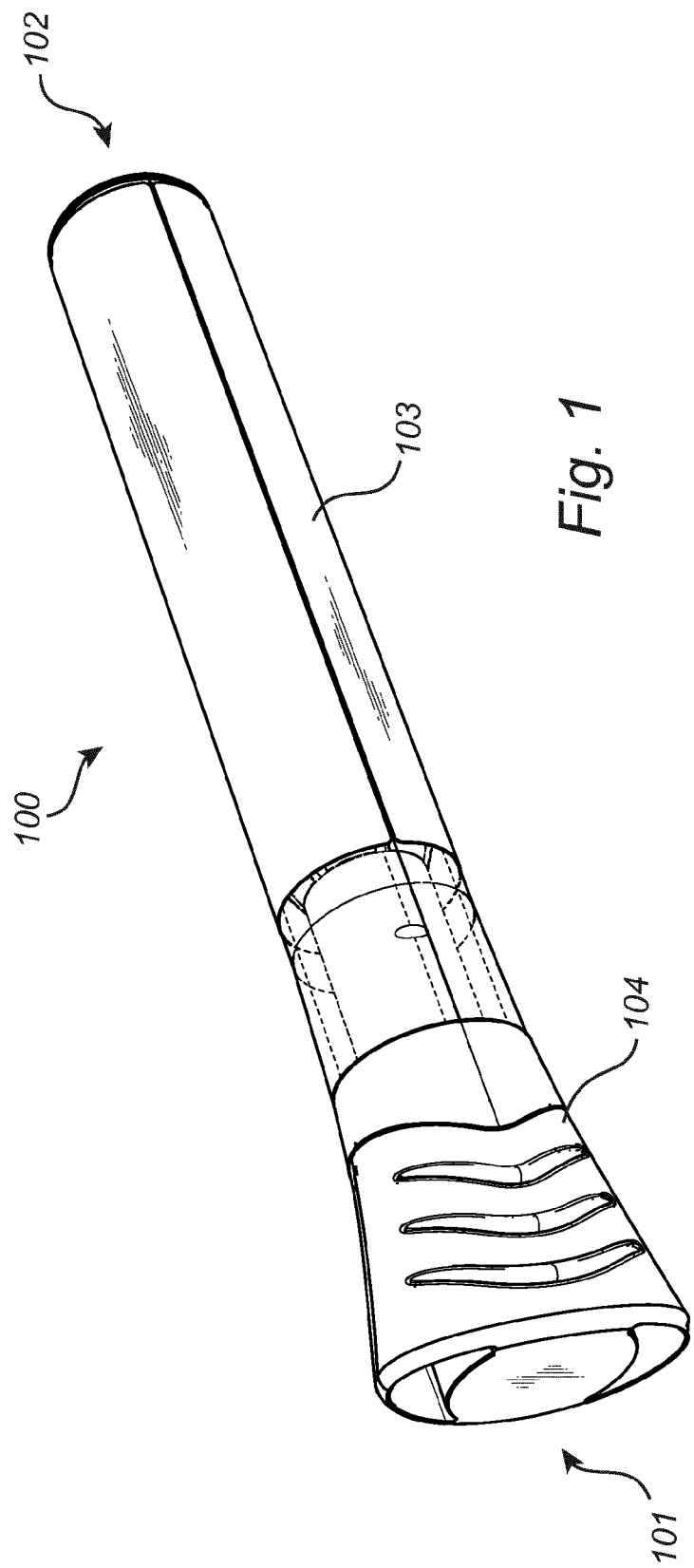
FIG. 1 is a schematic perspective view of an embodiment of the medicament delivery device according to the invention.

In a first embodiment of a medicament delivery device 100 according to the invention, as shown in FIG. 1, a medicament delivery device 100 having a proximal end 101 and a distal end 102. Concerning the terms "distal" and "proximal" they refer to points which are further away and closer to the injection site respectively. The medicament delivery device 100 comprises a housing made from e.g. thermoplastic and a front cap 104, also made from thermoplastic or similar.

Figure 2:
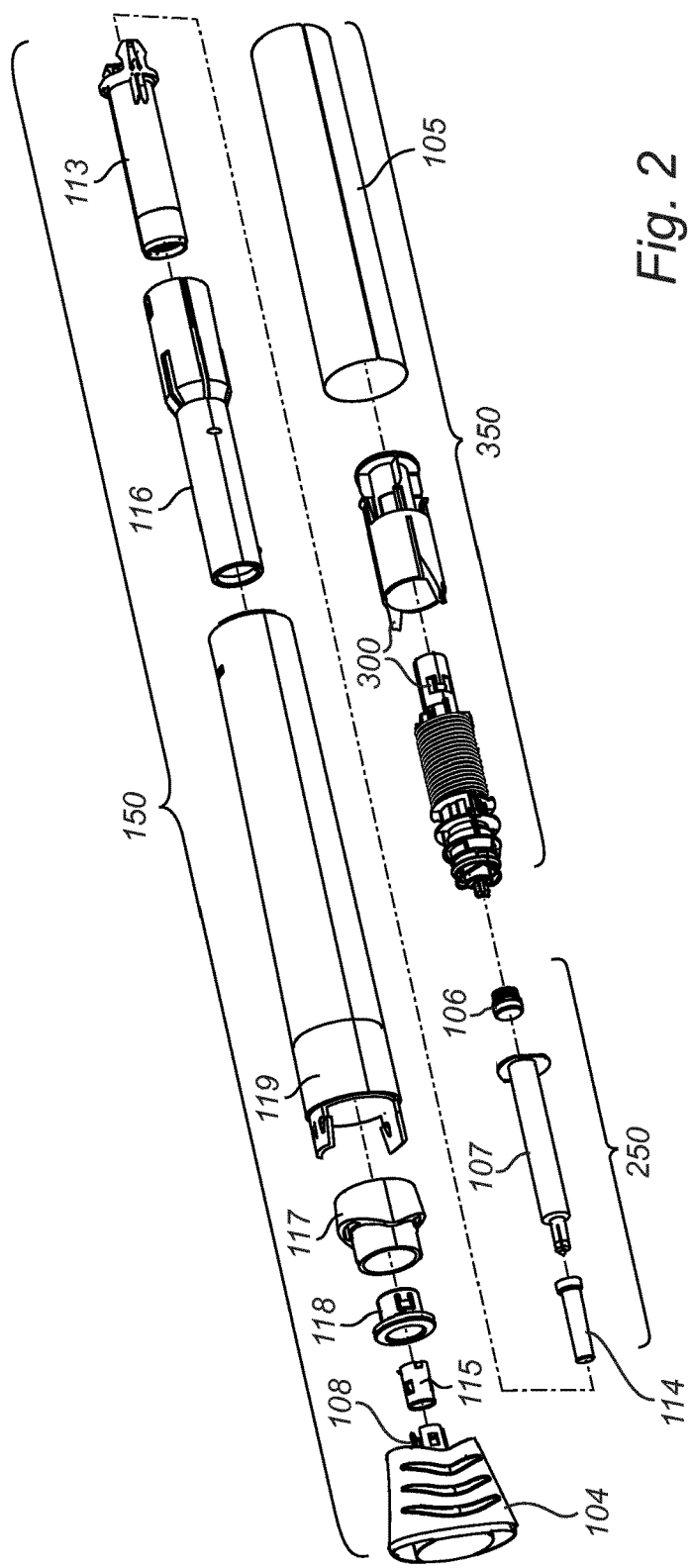
FIG. 2 is a schematic exploded perspective view of an embodiment of the medicament delivery device according to the invention.
Figure 3A:
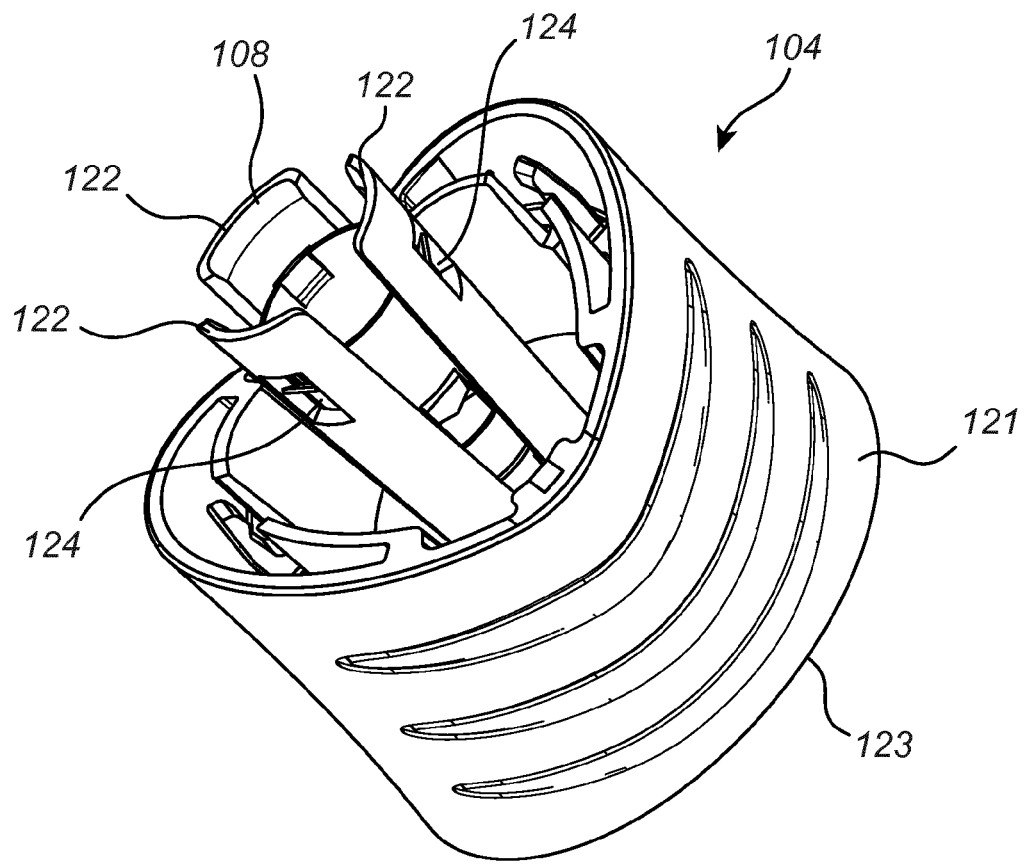
FIG. 3a-3c are schematic perspective views of an embodiment of the medicament delivery device according to the invention.
Figure 3B:
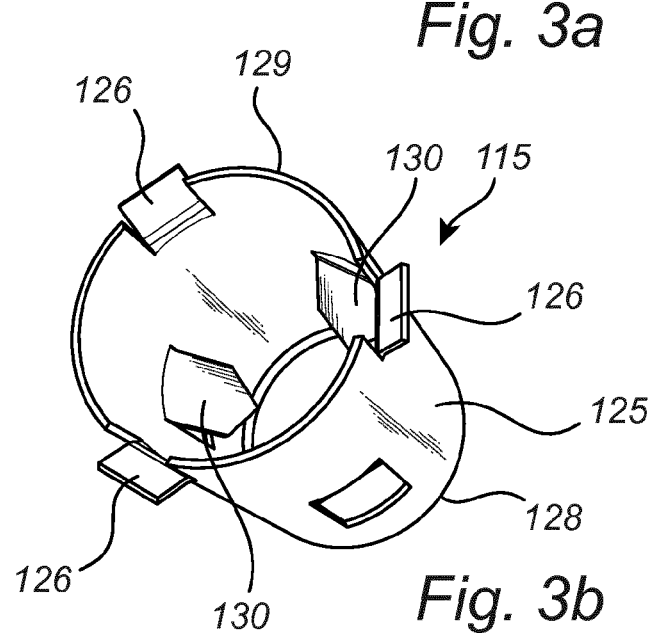
Figure 3C:
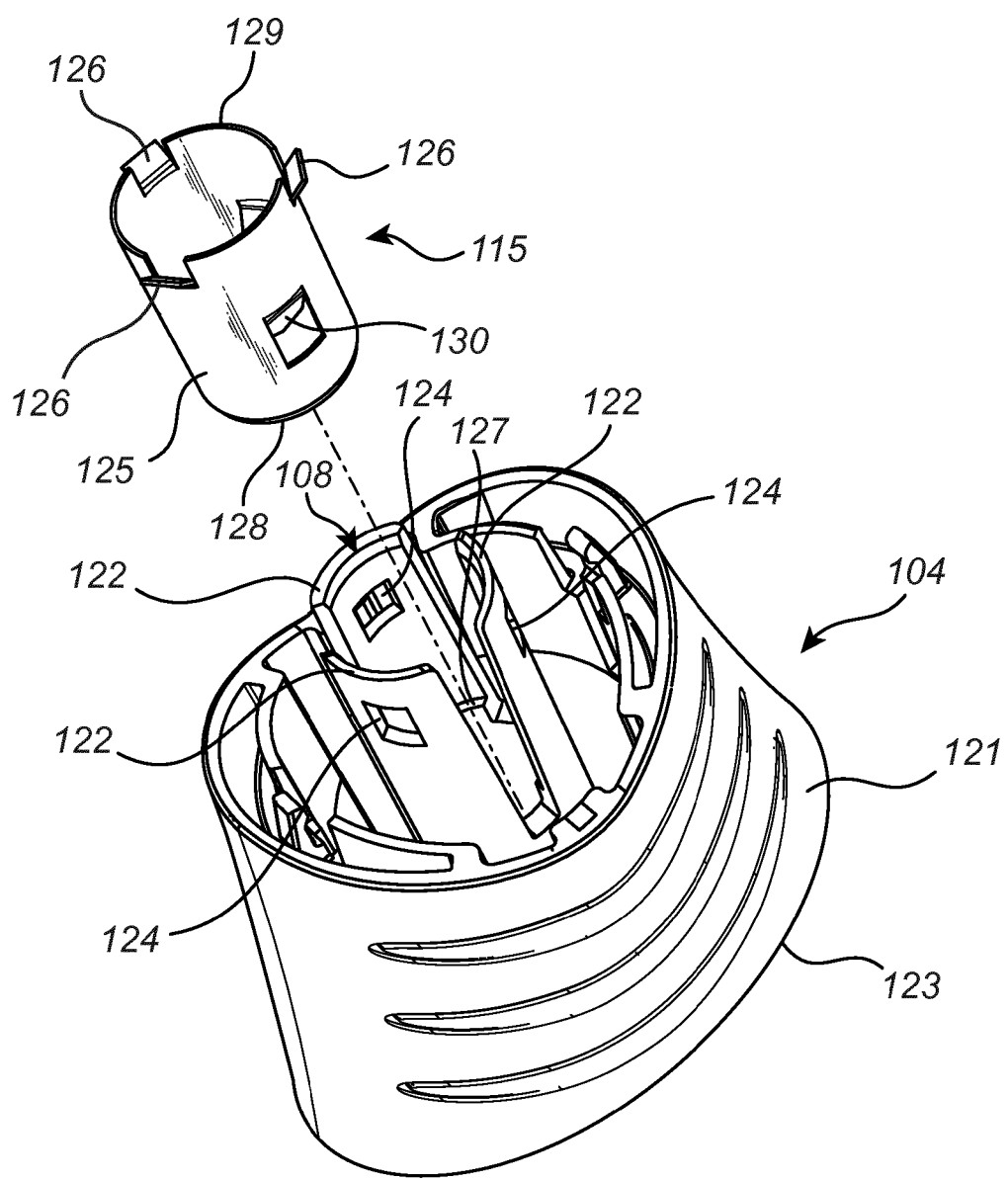

The building up of a medicament delivery device 100 according to the invention will now be described, referring to FIG. 2. FIG. 2 shows an exploded perspective view of a first embodiment of the medicament delivery device 100 in accordance with the present invention. The medicament delivery device 100 generally comprises three parts: A front part 150; a syringe part 250 and; a rear part 350. This means that during the final assembly of the medicament delivery device according to the present invention, these three parts are assembled.

Turning first to the rear part 350, this comprises an outer rear shell or a label 105 arranged to function as a grip surface for a user. To this end, the outer rear shell or label 105 could be provided with grip enhancing materials, such as rubber or similar, over at least parts thereof in order to provide for safe use of the medicament delivery device. Further, the rear part 350 comprises a drive mechanism 300 arranged to act on a plunger 106 provided within a medicament container, here represented as a syringe 107. No detailed description of how the drive mechanism functions will be given within this application since the skilled person realizes that there exist a large number of different drive mechanisms applicable to a medicament delivery device as described herein.

Figure 4:
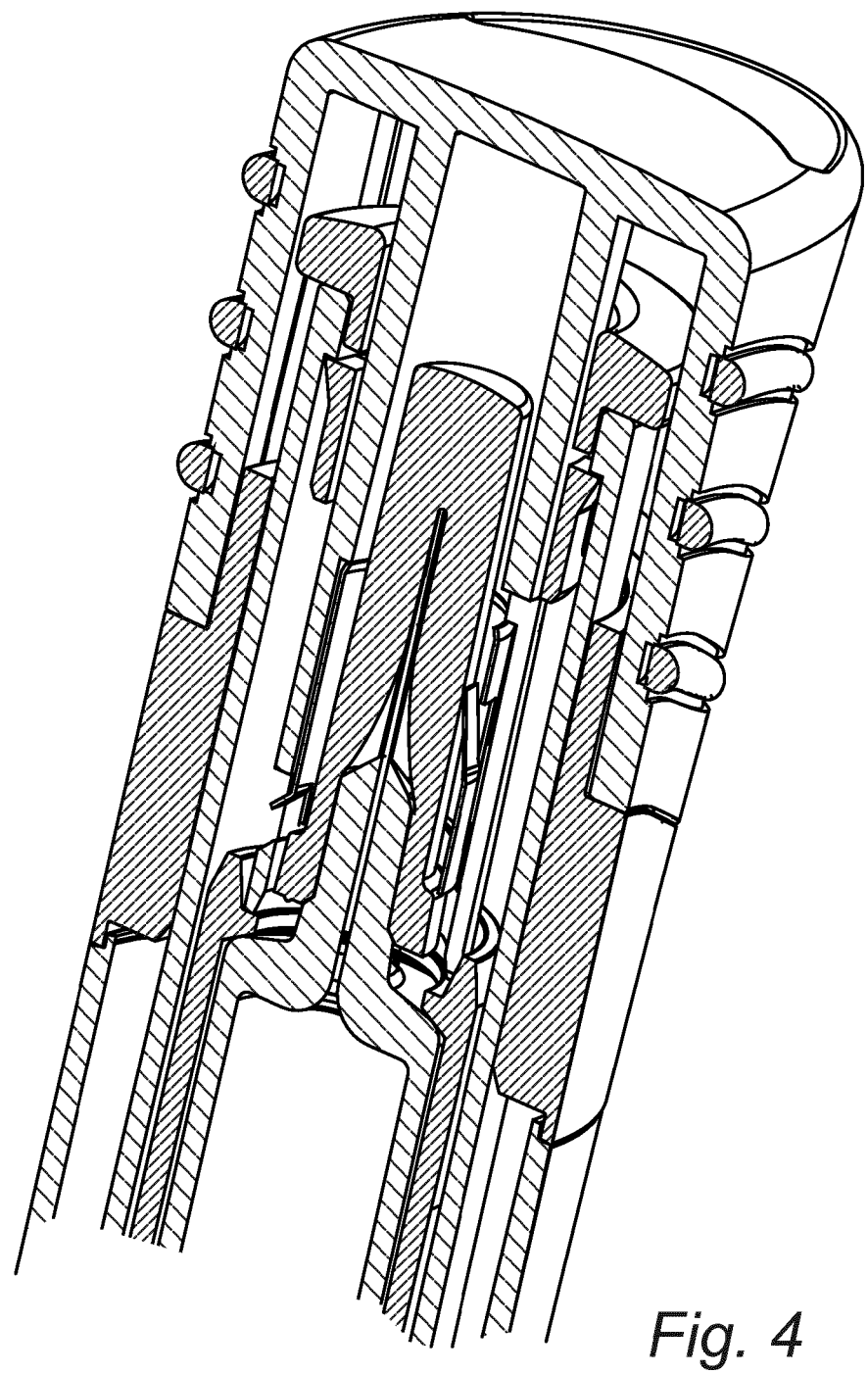
FIG. 4 is a schematic perspective cross-section of a detail of the medicament delivery device according to the invention.

The syringe part 250 comprises the syringe 107 within which plunger 106 is arranged and a needle 131 is arranged at a proximal end of syringe 107. In order to protect the needle 131 and ensure sterility of the needle 131, a needle shield 114 is arranged on the needle 131, FIGS. 2 and 4. In the shown embodiment the needle shield is a flexible needle shield (FNS) but it is also possible that the needle shield is a rigid needle shield (RNS).

The front part 150 comprises a front cap 104 having a shield grabber support 108 into which shield grabber support a shield grabber 115 can be inserted. Further, a front shell or housing 119 is provided and a movable needle cover 116 is arranged within said front shell or housing 119 and within the needle cover 116, in turn, is a movable syringe holder 113 arranged to receive and hold the syringe 107. The front part 150 further comprises a front end cover 117 which is provided at a proximal end of the front shell or housing 119 and is held in place by means of a snap-fit connection provided by connecting elements at a proximal end of front shell or housing 119 and corresponding connecting elements within front end cover 117. A front ring 118 is arranged and fixed to the needle cover 116 at a proximal end thereof. The front ring 118 comprises a flange at a proximal end thereof which, in a mounted state of the medicament delivery device 100, is arranged at a distance from a proximal end surface of the front end cover 117. When a user intends to deliver a medicament, the medicament deliver device 100 according to the invention is triggered by pushing the front ring 118 against a preferred part of the body. This will cause the front ring 118 to be axially displaced relative to the front end cover 117 until the front ring 118 reaches the proximal end surface of the front end cover 117. During this displacement, the needle cover 116 will be simultaneously displaced thus releasing the drive mechanism provided at the rear part 350 such that the medicament in syringe 107 is expelled through the needle 131 thereof.

The syringe, typically having a glass medicament container, is normally not rigidly mounted within the housing due to tolerance variations between the parts, especially glass containers of syringes often exhibit substantial tolerance variations, thus creating a certain amount of play between the syringe and the housing. If the medicament delivery device is e.g. dropped onto the floor, or otherwise subjected to an impact, especially to a rear end thereof, the syringe will move inside the medicament delivery device. The distance of movement will correspond to the amount of play between the housing and the syringe. If the shield grabber is rigidly arranged in the cap, i.e. no play between the two parts, the movement of the syringe could cause the needle shield to come loose from the needle 131 since the needle 131 is fixedly mounted to the syringe and will follow the movements thereof, thus compromising the sterility of the needle 131.

In FIGS. 3a-3c and 4, an embodiment of the front cap 104 of the present invention is shown. The front cap 104 comprises an outer shell 121, here shown having an elliptical cross-section. The skilled person, however, realizes the outer shell 121 can have any suitable cross-section. Provided inside the outer shell 121 is a shield grabber support 108 arranged to receive and hold a shield grabber 115. The shield grabber support 108 comprises three generally parallel tongues 122 extending in a direction parallel to a longitudinal axis of the medicament delivery device 100 to which the front cap 104 is intended to be connected. The tongues 122 of the shield grabber support 108 can extend individually all the way to a proximal end surface 123 of the front cap 104. To achieve a preferred balance between rigidity and flexibility of the tongues 122, it may however be more suitable to provide a proximal part of shield grabber support 108 in the form of a hollow or solid cylinder and only a distal part of the shield grabber support 108 in the form of resilient tongues 122. The exact disposition of these parts can be determined for each individual case. The tongues 122, in all, have a generally circular cross-section and are each provided with an aperture 124, preferably but not necessarily, near a distal end of the tongues 122. Shield grabber 115 has a generally circular cross-section and dimensioned to fit within, or between, the tongues 122. The fit should be such that the shield grabber 115 can move axially relative the shield grabber support 108. An excessively tight fit is therefore unwanted since this could prevent or at least hamper the axial movement of the shield grabber 115 relative to the shield grabber support. A certain amount of radial play between the shield grabber 115 and the shield grabber support 108 is acceptable but it should be restricted in order to prevent the shield grabber 115 from wedging and getting stuck within the shield grabber support 108. The cylindrically casing 125 of the shaped shield grabber 115 has three tabs 126 cut and folded outwardly therefrom. When the shield grabber 115 has been inserted into the shield grabber support 108, these tabs 126 will protrude through apertures 124 provided in the tongues 122. Due to the fact that the tabs 126 are folded outwardly from a distal end of the cylindrical casing 125, i.e. each tab 126 is folded towards a proximal end of the shield grabber 115, the tabs 126 will interact with a distal edge of a corresponding aperture 124 thus defining the distal end position of the axial movement of the shield grabber 115 within the shield grabber support 108. The proximal end position of the axial movement of the shield grabber 115 within the shield grabber support 108 can also be defined by the tabs 126. In a preferred embodiment, however, the proximal end position of the axial movement of the shield grabber 115 within the shield grabber support 108 is defined by a shelf-like circular abutment surface 127 provided on an inner surface of the shield grabber support 108 against which a proximal end surface 128 abuts in the proximal end position of the axial movement of the shield grabber 115 within the shield grabber support 108. In comparison with the embodiment where the tabs 126 define the proximal end position, this embodiment provides a more defined and rigid end position. The total relative axial movement, i.e. axial play, between the shield grabber 115 and the shield grabber support 108 can typically amount to 0.5 mm to 4 mm and more specifically to about 1 mm to 2 mm. This is enough to cover the play between the front part 150 and the syringe part 250 such that the sterility of the needle is not jeopardized in case of a sudden impact to the rear part 350 of the medicament delivery device 100.

The shield grabber 115 further comprises three inwardly folded hook elements in the form of tabs 130 being cut and folded inwardly from said casing 125. These tabs 130 are each provided with a pointed tip directed towards proximal end surface 128 of the shield grabber 115. The front cap is configured to be releasably connected to the medicament delivery device. More particularly, the front cap 104 is configured to be fitted to a front/proximal end part of a medicament delivery device. Thus, the front cap 104 comprises a space arranged to receive the front end part of a medicament delivery device. The space of the front cap 104 is arranged between the outer surface of the shield grabber support 108 and an inner surface of an internal wall of the front cap 104. The fit should be such that the front cap can be removed by pulling and/or rotating said cap relative the front end part of a medicament delivery device. In the shown embodiment, the front cap is fitted to the front end cover 117. When the front cap 104 provided with a shield grabber 115 is fitted to the front end cover 117, the tabs 130 will interact with the needle shield 114 of the syringe 107 and function as barbs, i.e. they will slide over the outer surface of the needle shield 114 when the front cap 104 is moving in a direction from a proximal end towards a distal end, e.g. during mounting to the medicament delivery device 100, but as soon as the front cap 104, and thus the shield grabber 115 is moved towards a proximal position the tabs 130 will cut into the needle shield 114. Therefore, the needle shield 114 can be loosened from the needle 131 by pulling the front cap 104. If the medicament delivery device 100 according to the present invention is dropped on its distal end 102, the syringe 107, due to the inherent play, will be forced to move towards the distal end 102 of the medicament delivery device thus forcing the tabs 130 to cut into the outer surface of the needle shield 114. However, due to the fact that the shield grabber 115 has been pushed onto the needle shield by an axial movement of the front cap 104 towards a distal end position of the medicament delivery device 100, the shield grabber 115 will be at, or at least close to, its proximal end position, shown in FIG. 4. This means that if the syringe moves towards a more distal position, bringing the shield grabber 115 with it, the shield grabber 115 will have all, or at least most of, its axial play to compensate for this movement without the needle shield 114 having to move relative to the needle 131 so that the sterility of the needle 131 can be ensured at all times. Preferably, the shield grabber 115 is made from metal which ensures light weight, and sufficient rigidity of the shield grabber 115.

Finally, it is realized that a front cap according to the present invention includes a number of advantages over the prior art solutions. The axial movability of the shield grabber relative the shield grabber support ensures the preservation of the sterility of the needle in case the medicament delivery device is subjected to an impact at the rear, or distal, end thereof. It should be noted that an impact to a front, or proximal, end thereof is less of a problem since that will only force the needle shield towards the needle of the syringe. Therefore, mainly the effect of impacts at the rear end thereof is relevant to reduce. Also the fact that the solution is concentrated to the front cap is beneficial, no major change need be done to the rest of the medicament delivery device.

It is to be understood that the embodiments described above and in the drawings are to be regarded only as non-limiting examples of the invention and that they may be modified in many ways within the scope of the claims.

The invention claimed is:

1. A front cap for a medicament delivery device having a proximal end and a distal end, the front cap being configured for releasable connection to the medicament delivery device and comprising a shield grabber support and a shield grabber configured to connect the front cap to an outer surface of a needle shield of a syringe in the medicament delivery device, wherein the shield grabber is made of metal and is coupled to the shield grabber support such that the shield grabber is axially movable relative to the shield grabber support; the shield grabber is axially movable between a distal end position and a proximal end position; the distal end position is defined by a protruding element provided at the shield grabber and a stop surface provided at the shield grabber support against which the protruding element abuts in the distal end position; the shield grabber has a casing having a substantially hollow cylindrical cross-section arranged to fit inside the shield grabber support; wherein an inside of the shield grabber includes a hook element arranged to cut into an outer wall surface of the needle shield at a point between proximal and distal ends of the needle shield, wherein the hook element is arranged to slide over the outer wall surface of the needle shield when the front cap is moving in a direction from the proximal end towards the distal end, but as soon as the front cap and the shield grabber are moved towards a proximal position the hook element cuts into the needle shield, wherein the hook element comprises a tab cut and folded inwardly from the casing, wherein the protruding element comprises a tab cut and folded outwardly from the casing, and wherein the tab of the hook element is positioned proximally relative to the tab of the protruding element.

2. The front cap of claim 1, wherein the proximal end position is defined by an abutment surface provided on an inner side of the shield grabber support against which an end surface of the shield grabber abuts in the proximal end position.

3. The front cap of claim 2, wherein the shield grabber support has a substantially hollow cylindrical cross-section, and the abutment surface is a circular surface on an inner surface of the shield grabber support.

4. The front cap of claim 1, wherein the shield grabber support comprises an aperture therein, and a distal edge formed in the shield grabber support by the aperture defines the stop surface against which the protruding element of the shield grabber abuts in the distal end position.

5. The front cap of claim 4, wherein the shield grabber support comprises a plurality of tongue-shaped elements arranged in a generally circular manner, and the aperture is provided in at least one of the plurality of tongue-shaped elements.

6. The front cap of claim 1, wherein the shield grabber is axially movable a distance relative to the shield grabber support.

7. The front cap of claim 6, wherein the distance is between the proximal end position and the distal end position and is 0.5 millimeter (mm) to 4 mm.

8. The front cap of claim 6, wherein the distance is between the proximal end position and the distal end position and is 1 millimeter (mm) to 2 mm.

9. The front cap of claim 1, wherein the shield grabber is arranged to be inserted into the shield grabber support and secured therein by a snap-fit.

10. A medicament delivery device, comprising a syringe having a medicament container, a needle, a needle shield, a drive mechanism arranged to act on a plunger in the medicament container for expelling a medicament, and a front cap according to claim 1.

* * * * *